Jan. 3, 1961 R. S. MOORE Plant Pat. 2,009

MINIATURE ROSE PLANT

Filed March 21, 1960

WITNESS

Addison E. Avery

INVENTOR

Ralph S. Moore

Webster & Webster

ATTYS.

United States Patent Office

Plant Pat. 2,009
Patented Jan. 3, 1961

2,009

MINIATURE ROSE PLANT

Ralph S. Moore, Visalia, Calif.

Filed Mar. 21, 1960, Ser. No. 16,620

1 Claim. (Cl. 47—61)

This invention relates to a new and distinct variety of hybrid miniature rose plant of hardy, upright, much branched, dwarf, bush type, which bears attractive rose-pink flowers having very double petalage.

As compared to the Dian miniature rose (United States Plant Patent No. 1808), and to which in general it most nearly resembles, the present variety is distinctively characterized:

By a faster growing, taller, and larger plant which is more upright, has heavier canes, and a greater number of thorns.

By glossy green foliage which commonly holds into the winter season, and which foliage has a tendency to shade to bronze-green; young leaves and new shoots frequently being reddish or bronze-green.

By rooting very readily from both soft and hard wood cuttings.

And by flowers which are slightly larger, held erect on very stiff stems, and a deeper rose-pink when fully open, and then—in shape—resembling a pompon chrysanthemum.

The variety was originated by me, in my nursery located at Visalia, California, and under conditions of careful control and observation, as a cross between two unnamed seedlings; the parent seedling having been *Rosa wichuraiana* × Floradora, while the pollen seedling was Oakington Ruby × Floradora—all unpatented.

Subsequent to origination of the variety I successfully asexually reproduced it, in my nursery located as aforesaid, by budding as well as cuttings; the reproductions having run true in all respects.

Figure 1:
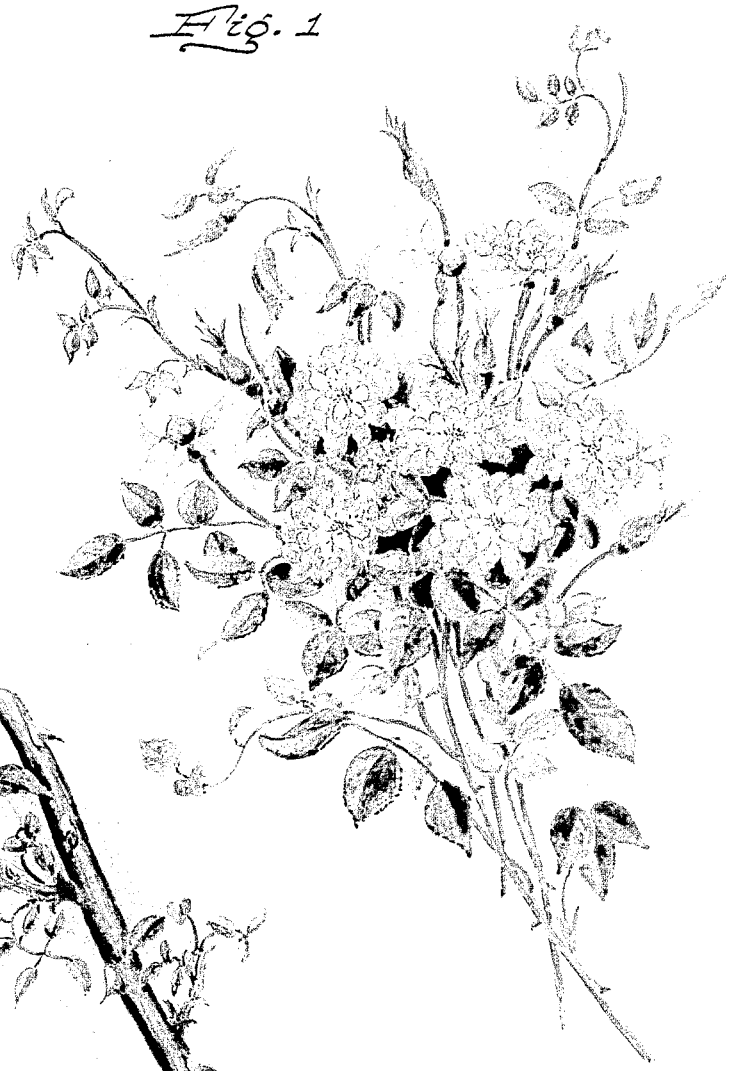

Fig. 1 of the drawings illustrates a spray, including foliage, buds, and flowers.

Figure 2:
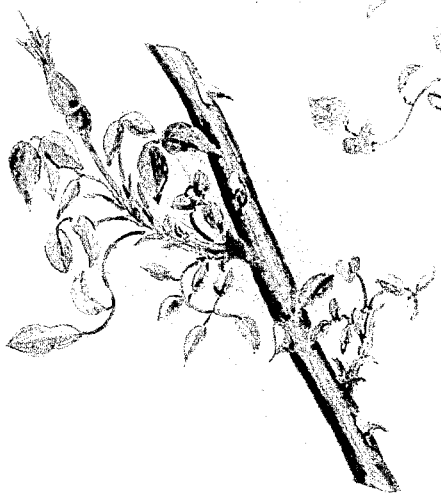

Fig. 2 is a view showing a portion of a branch, and illustrates particularly new shoots and thorns.

Referring now specifically to the new and distinct variety of miniature rose plant, the following is a detailed description thereof in outline; all major color plate identifications being—as indicated—either by reference to The British Colour Council Horticultural Colour Chart, or Maerz and Paul Dictionary of Color, except where common terms of color definition are employed.

Type: Hardy; dwarf; bush; seedling; greenhouse; cut flowers; outdoors; garden decoration.
Class: Hybrid miniature.

*Flowers*

Continuity: Intermittent to continuous.
Fragrance: Slight moderate; fruit.
Flowers borne: Singly to several to stem, in rounded cluster on strong, medium length stems.
Quantity of bloom: Free, both outdoors and in greenhouse.
Bud:
*Peduncle.*—Short to medium length; heavy; erect; stiff; dark reddish-green; smooth.
*Before calyx breaks.*—Size—small. Form—pointed, with foliaceous appendages on the surface of the bud, and with foliaceous parts extending beyond the tip of the bud equal to one-half to three-fourths of its length. Color—green.
*As calyx breaks.*—Color—Spirea Red (025 British Colour Council).
*As first petal opens.*—Size—small. Form—globular. Color—Spirea Red (025/1 British Colour Council). Opening—always opens well.

Bloom:
*Size when fully open.*—Small, averaging 1″ to 1¼″, although sometimes up to 1½″.
*Petalage.*—Very double, with from 40 to 60 petals arranged regularly.
*Form.*—Flat; sometimes slightly cupped; very loosely rolled outward at maturity.
Petals: Thick; satiny both inside and outside.
*Shape.*—Outside—obovate, with acute tip (or broad lanceolate with acute tip). Intermediate—lanceolate. Inside—lanceolate.
*Color.*—Newly opened flower from plant grown outdoors (early October)—Outside petal; outer surface—Spirea Red (025/1 British Colour Council); inside surface—Spirea Red (025 British Colour Council). Intermediate petal: outside surface—Spirea Red (025/1 British Colour Council); inside surface—Spirea Red (025 British Colour Council). Inner petal: outside surface—Spirea Red (025/2 British Colour Council); inside surface—Spirea Red (025/2 British Colour Council). A flower that was open for three days outdoors (early October)—All petals: outside surface—Magenta Rose (27/3 British Colour Council); inside surface—Magenta Rose (27/2 to 27/3 British Colour Council).
*General color effect.*—Rose-pink, darkening somewhat in cool weather. All petals shade to white (9–A–1 Maerz and Paul), or near white at the base. The center of the flowers have a tint of yellow (9–G–4 Maerz and Paul).
*Behavior.*—Drop off cleanly.
*Flower longevity (October).*—Bush in garden—four to five days or longer. Cut flowers kept at living room temperatures—three to four days.
Reproductive organs:
*Stamens.*—Usually none.
*Pollen.*—None.
*Pistils.*—Medium number.
*Styles.*—Even; short; heavy; bunched.
*Stigma.*—Yellow or brownish yellow.
*Ovaries.*—All enclosed in calyx.
*Hips.*—None.
*Sepals.*—Permanent; long; spear-shaped. Color—dark green.
*Seeds.*—None.

*Plant*

Foliage:
*Leaves.*—Compound of five to seven leaflets; normal abundance; small to medium; leathery; glossy.
*Leaflets.*—Shape—lanceolate with apex acute and base round. Margin—serrate.
*Color.*—Upper surface—medium to dark green (23–L–7 Maerz and Paul). under surface—lighter green (22–H–5 Maerz and Paul). The leaves, on occasion, have a tendency to shade to bronze (7–J–9 Maerz and Paul), producing a bronze-green effect.
*Rachis.*—Heavy; upper side grooved, hairy; under side moderately thorny.
*Stipules.*—Medium to long; medium width; with long points turning out at an angle of less than 45 degrees.

Growth:

*Habit.*—Dwarf; bushy; upright; much branched.

*Growth.*—Vigorous.

*Canes.*—Medium to heavy for the type of plant.

*Main stems.*—Color—green (23–L–12 Maerz and Paul). Thorns—color—tan (6–A–11 Maerz and Paul); several; medium length; hooked downward, with oval base. Prickles—none. Hairs—none.

*Branches.*—Color—green. Thorns—several; medium length; hooked downward, with oval base. Prickles—none. Hairs—none.

*New shoots.*—Color—bright green, but frequently reddish or bronze-green, which colors are also present on the young leaves (see Fig. 2). Thorns—several; medium length; hooked downward, with oval base. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of rose plant of the hybrid miniature class and hardy, dwarf, bush type, characterized—as compared to the Dian miniature rose plant, and which it most nearly resembles—by a faster growing, taller, larger and more upright plant; by glossy green foliage which commonly holds into the winter season, and has a tendency to shade to bronze-green, with new shoots and young leaves frequently a reddish or bronze-green; by rooting very readily from both soft and hard wood cuttings; and by slightly larger rose-pink flowers which are a deeper shade when fully open and which then resemble a pompon chrysanthemum, the flowers being held erect on very stiff stems.

No references cited.